United States Patent [19]

Waldmann et al.

[11] 4,013,723
[45] Mar. 22, 1977

[54] PROCESS FOR PREPARING ALDEHYDES

[75] Inventors: Helmut Waldmann; Wulf Schwerdtel, both of Leverkusen; Wolfgang Swodenk, Odenthal-Globusch, all of Germany

[73] Assignee: Bayer Aktiengesellschaft, Leverkusen, Germany

[22] Filed: Dec. 27, 1972

[21] Appl. No.: 318,965

[30] Foreign Application Priority Data

Jan. 13, 1972 Germany .......................... 2201455

[52] U.S. Cl. .......................... 260/601 R; 260/598; 260/599; 260/600 R; 260/602; 260/348 C

[51] Int. Cl.² ................. C07C 45/22; C07C 47/12; C07C 47/14; C07C 47/28

[58] Field of Search .................................. 260/601

[56] References Cited

OTHER PUBLICATIONS

J. Hoffman, J., JACS, vol. 79, pp. 503–504 (1957).

*Primary Examiner*—Donald G. Daus
*Assistant Examiner*—David B. Springer
*Attorney, Agent, or Firm*—Burgess, Dinklage & Sprung

[57] ABSTRACT

Aldehydes are prepared by reacting an oxirane compound with hydrogen peroxide in the presence of one or more compounds of a metal of Groups IIIa-VIIa or Group VIII of the Mendeleev period table.

5 Claims, No Drawings

PROCESS FOR PREPARING ALDEHYDES

This invention relates to a process for the preparation of aldehydes from oxirane compounds and hydrogen peroxide.

Aldehydes are important intermediate products for the synthesis of medicaments or azo dyes. Also certain aldehydes, e.g. glutaric dialdehyde, are used as tanning agents.

It is known that aldehydes can be produced by first preparing the corresponding 1,2-diols from certain oxirane compounds and then splitting the diols into the corresponding aldehydes in a second stage by reacting them with compounds such as lead tetraacetate (R. Criegee, Ber. d. dtsch. chem. Ges. 64, 264 (1931)) or periodic acid (L. Malaprade, Bull. Soc. Chim. France (4) 43, 683, (1928).

The disadvantage of this method is, first, that the 1,2-diols must initially be prepared as intermediate compounds and, second, that the oxidising agent, such as lead tetraacetate or periodic acid, which is used in the second stage does not act as a catalyst but takes a direct part in the reaction. The reaction products of the oxidising agents used for decomposing the 1,2-diols must, therefore, be isolated at the end of the reaction or reconverted into the oxidising starting compounds before they can be used again.

SUMMARY

It has now been found that aldehydes can be obtained by a technically advantageous process in which oxirane compounds are reacted with hydrogen peroxide, the reaction taking place with the addition of a compound of a metal of the Groups IIIa-VIIa or Group VIII of the periodic system of elements (Mendeleev), optionally with the addition of a compound of an alkali metal.

DESCRIPTION

The oxirane compounds suitable for the process according to the invention have the following general formula I:

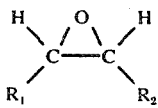

in which $R_1$ and $R_2$ represent, independently of each other, hydrogen, a phenyl group optionally substituted by fluorine, chlorine, CN, bromine, $C_1$-$C_6$ alkoxy, alkyl or oxiranyl, a straight chain or branched chain alkyl radical optionally substituted by fluorine, chlorine, bromine, OH, $C_1$-$C_6$ alkoxy, carbo-$C_1$-$C_3$-alkoxy, CN, phenyl or oxiranyl, or a cycloalkyl radical optionally substituted by fluorine, chlorine, bromine, OH, alkyl, $C_1$-$C_6$ alkoxy, carbo-$C_1$-$C_3$-alkoxy, phenyl or oxiranyl; in addition, the radicals $R_1$ and $R_2$ together with the C-atoms of the oxirane ring may represent a carbocyclic ring having up to 24 C-atoms optionally substituted by fluorine, chlorine, bromine, OH, alkyl, phenyl, $C_1$-$C_6$ alkoxy, carbo-$C_1$-$C_3$- alkoxy or CN.

The following are specific examples of substituted phenyl groups:

4-chlorophenyl, 2,4-dichlorophenyl, 4-methoxyphenyl, 4-chloro-2-methoxyphenyl, 4-propoxyphenyl, 4-tert.-butoxyphenyl, 4-n-hexoxyphenyl, 4-bromo-3,5-di-tert.-butylphenyl, 4-cyanophenyl and 4-cyano-3,5-dimethylphenyl.

The following are specific examples of straight chain or branched chain alkyl radicals:

methyl, ethyl, propyl, n-butyl, isobutyl, tert.-butyl, pentyl, hexyl, heptyl, octyl, nonyl, decyl, undecyl, dodecyl, pentadecyl, hexadecyl, octadecyl and their isomers.

The following are examples of substituted alkyl radicals:

chloromethyl, β-chloroethyl, β-ethylhexyl, isopropyl-3-bromobutyl, hydroxymethyl, β-hydroxyethyl, W-hydroxyhexyl, 2-hydroxymethylhexyl, β-methoxyethyl, 3-propoxypropyl, n-hexoxymethyl, 2,4,6-trimethoxyhexyl, 2-(methoxymethyl)-propyl, (carbomethoxy)-methyl, 3-(carbopropoxy)-propyl, 3-(carbomethoxy)-hexyl, 3-(β-carbomethoxyethyl)-butyl, β-cyanoethyl, 2-(β-cyanoethyl)-propyl, W-cyanoheptyl and W-cyanooctyl.

The following are examples of phenyl groups substituted by an alkyl radical:

tolyl, ethyl phenyl, propylphenyl, n-butylphenyl, tert.-butyl-phenyl, di-tert.-butylphenyl and tri-tert.-butylphenyl.

The following are examples of alkyl radicals substituted by a phenyl radical:

phenylmethyl, phenylethyl, phenylpropyl, phenyl-tert.-butyl and W-phenylhexyl.

The following are examples of oxirane compounds:
2,3-dimethyloxirane, 2-methyl-3-ethyloxirane, 2-methyloxirane, 2-ethyloxirane, 2-n-butyloxirane, 2-isobutyloxirane, 2-tert.-butyloxirane, 2-phenyloxirane, 2-pentyloxirane, 2,3-diethyloxirane, 2,3-dihexyloxirane, 2-ethyl-3-hexyloxirane, 2,3-dioctyloxirane, 2-(2-ethyl)-hexyl-3-methyloxirane, 2-nonyl-3-methyloxirane, 2,3-diisopropyloxirane, 2,3-diundecyloxirane, 2,3-didodecyloxirane, 2-pentadecyl-3-hexyloxirane, 2-hexadecyl-3-octadecyloxirane, 2-(β-ethylbutyl)-3-(α-ethylbutyl)-oxirane, 2,3-di-(3-pentylhexyl)-oxirane, 2-chloromethyloxirane, 2-(β-chloroethyl)-oxirane, 3-(γ-chloropropyl)-oxirane, 2-chloromethyl-3-methyloxirane, 2,3-dichloro-oxirane, 2,3-di-(β-chloroethyl)-oxirane, 2,3-di-(γ-chloropropyl)-oxirane, 2,3-di-(α-chloro-n-butyl)-oxirane, 2-fluoromethyloxirane, 2,3-trifluoromethyloxirane, 2,3-di-(β-hydroxyethyl)-oxirane, 2,3-di-(γ-hydroxypropyl)-oxirane, 2,3-dimethoxy-oxirane, 2,3-di(β-methoxyethyl)-oxirane, 2-(γ-propoxypropyl)-3-propyl-oxirane, 2,3-di-(β-hexoxyethyl)-oxirane, 2,3-di-(carbomethoxymethyl)-oxirane, 2,3-di-carboxethoxy-oxirane, 2,3-di-(carboisopropoxymethyl)-oxirane, 2,3-di-(β-cyanoethyl)-oxirane, 2,3-di-(β-phenylethyl)-oxirane, phenyloxirane, 2,3-diphenyloxirane, 2,3-di-(p-chlorophenyl)-oxirane, 2,3-di-(p-fluorophenyl)-oxirane, 2,3-di-(2,4-dichlorophenyl)-oxirane, 2,3-di-(4-bromo-3,5-di-tert.-butylphenyl)-oxirane, 2,3-di-(4-cyanophenyl)-oxirane, 2,3-di-(4-methoxyphenyl)-oxirane, 2,3-di-(2,4-isopropoxyphenyl)-oxirane, 2,3-di-(4-hexoxyphenyl)-oxirane, 2,3-di-(2,4-dimethylphenyl)-oxirane, 2,3-di-(4-tert.-butyl-phenyl)-oxirane, 2-(4-oxiranylphenyl)-oxirane, 2-(2-oxiranylphenyl)-oxirane, 2-(oxiranylmethyl)-oxirane, 2-(β-oxiranylethyl)-oxirane, cyclobutyloxirane, 2,3-dicyclobutyloxirane, 2,3-dicyclopentyl-oxirane, 2,3-dicyclohexyloxirane, cyclohexyloxirane, 2-cyclohexyl-3-methyloxirane, 2,3-di(α-chlorocyclohexyl)-oxirane, 2,3-di-(α-methoxycyclopentyl)-oxirane, 2,3-di-(β-propoxycyclohexyl)-oxirane, 2,3-di-(α-carboisopropoxy-cyclopentyl)-oxirane, 2,3-di-(α- cyanocyclododecenyl)-oxirane, α-cyanocyclopentyl-oxirane, β-cyanocyclopentyl-oxirane, 2,3-di-(β-cyanocyclohexyl)-oxirane, 2,3-di-(β-fluorocyclohexyl)-oxirane, 2,3-di-(trifluoromethyl-cyclohexyl)-oxirane, (4-oxiranylcyclohexyl)-oxirane and (3-oxiranyl-cyclopentyl)-oxirane.

Another preferred group of compounds of the general formula (I) corresponds to the following formula (II):

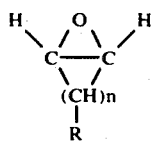

(II)

wherein n represents an integer of from 3 to 10 and each of the C-atoms determined by n is substituted by R independently of the others, R representing hydrogen, fluorine, cyanide, $C_1$-$C_6$ alkoxy, $C_1$-$C_6$ alkyl, $C_5$-$C_7$ cycloalkyl or a phenyl group optionally substituted by fluorine, chlorine, cyanide or $C_1$-$C_6$ alkoxy.

The following are specific examples: cyclopentenoxide-(1,2), 3-chlorocyclopentenoxide-(1,2), 3,5-dichlorocyclopentenoxide-(1,2), 4-hydroxycyclopentenoxide-(1,2), 3,5-dimethylcyclopentenoxide-(1,2), 3,5-diethylcyclopentenoxide-(1,2), 4-isopropylcyclopentenoxide-(1,2), 4-tert.-butyl-cyclopentenoxide-(1,2), 3,5-diphenylcyclopentenoxide-(1,2), 3,5-di-(4-chlorophenyl)-cyclopentenoxide-(1,2), 4-phenylcyclopentenoxide-(1,2), 3-methoxycyclopentenoxide-(1,2), 4-propoxycyclopentenoxide-(1,2), 3,5-diisopropoxycyclopentenoxide-(1,2), 4-tert.-butoxycyclopentenoxide-(1,2), 4-n-hexoxycyclopentenoxide-(1,2), 3-carbomethoxycyclopentenoxide-(1,2), 4-carbopropoxycyclopentenoxide-(1,2), 3,5-di-[(β-carbomethoxy)-ethyl-]cyclopentenoxide-(1,2), 3-cyanocyclopentenoxide-(1,2), 4-cyanocyclopentenoxide, 4-(β-cyanoethyl)-cyclopentenoxide-(1,2), 3-fluorocyclopentenoxide-(1,2), 3-trifluoromethylcyclopentenoxide-(1,2), cyclohexenoxide, 3-fluorocyclohexenoxide-(1,2), 3-trifluoromethyl-cyclohexenoxide-(1,2), 3-chlorocyclohexenoxide-(1,2), 4-chlorocyclohexenoxide-(1,2), 5-chlorocyclohexenoxide-(1,2), 4,5-dichlorocyclohexenoxide-(1,2), 3-hydroxycyclohexenoxide-(1,2), 3,6-dihydroxycyclohexenoxide-(1,2), 3-methylcyclohexenoxide-(1,2), 4-methylcyclohexenoxide-(1,2), 5-ethylcyclohexenoxide-(1,2), 3,5-diisopropylcyclohexenoxide-(1,2), di-n-hexylcyclohexenoxide-(1,2), 4-phenylcyclohexenoxide-(1,2), 4,5-diphenylcyclohexenoxide-(1,2) and 4-(p-chlorophenyl)-cyclohexenoxide-(1,2), 3-methoxycyclohexenoxide-(1,2), 4-ethoxycyclohexenoxide-(1,2), 4-isopropoxycyclohexenoxide-(1,2), 4-hexoxycyclohexenoxide-(1,2), 4-(β-cyanoethyl)-cyclohexenoxide-(1,2), cycloheptenoxide, 3-methylcycloheptenoxide-(1,2), 3,7-dimethylcycloheptenoxide-(1,2), 4,5,6-trimethylcycloheptenoxide-(1,2), 5-isopropylcycloheptenoxide-(1,2), 5-tert.-butylcycloheptenoxide-(1,2), 3-chlorocycloheptenoxide, 4-(β-chloroethyl)-cycloheptenoxide-(1,2), 4,6-dichlorocycloheptene-(1,2), 5-hydroxycycloheptenoxide-(1,2), 4,6-dihydroxycycloheptenoxide-(1,2), 3-phenylcycloheptenoxide-(1,2), 5-phenylcycloheptenoxide-(1,2), 4,6-di-(p-tert.-butylphenyl)-cycloheptenoxide-(1,2), 3-methoxycycloheptenoxide-(1,2), 5-methoxycycloheptenoxide-(1,2), 3-propoxycycloheptenoxide-(1,2), 5-tert.-butoxycycloheptenoxide-(1,2), 3-carbomethoxycycloheptenoxide-(1,2), 4-carbomethoxycycloheptenoxide-(1,2), 3,7-dicarbomethoxycycloheptenoxide-(1,2) and 5-(β-carbomethoxy)-ethylcycloheptenoxide-(1,2); cyclooctenoxide, 3-chlorocyclooectenoxide-(1,2), 6,7-dichlorocyclooctenoxide-(1,2), 6-hydroxycyclooctenoxide-(1,2), 3-methylcyclooctenoxide-(1,2), 6,7-dimethylcyclooctenoxide-(1,2), 4,8-dimethylcyclooctenoxide-(1,2), 6-phenylcyclooctenoxide-(1,2), 6-(p-chlorophenyl)-cyclooctenoxide-(1,2), 3-methoxycyclooctenoxide-(1,2), 4,7-dimethoxycyclooctenoxide-(1,2), 3-carbomethoxycyclooctenoxide-(1,2), 6,7-dicarbomethoxycyclooctenoxide-(1,2), cyclodecenoxide, 3-chlorocyclodecenoxide-(1,2), 3,10-dichlorocyclodecenoxide-(1,2), 6,7-dichlorocyclodecenoxide-(1,2), 3,4,8,9-tetrachlorocyclodecenoxide-(1,2), 6-hydroxycyclodecenoxide-(1,2), 3-methylcyclodecenoxide-(1,2), 3,10-dimethyl-cyclodecenoxide-(1,2), 6,7-dimethylcyclodecenoxide-(1,2), 6-phenylcyclodecenoxide-(1,2), 3-carbomethoxycyclodecenoxide-(1,2), 3,10-dicarboethoxycyclodecenoxide-(1,2), 6-carbopropoxycyclodecenoxide-(1,2), 3-cyanocyclodecenoxide-(1,2), 6,7-dicyanocyclodecenoxide-(1,2), cyclododecenoxide, 1-chlorocyclododecenoxide-(1,2), 4,5-dichlorocyclododecenoxide-(1,2), 5,6,9,10-tetrachlorododecenoxide-(1,2), 3,5,6,9,10,12-hexachlorododecenoxide-(1,2), 3-methyldodecenoxide-(1,2), 4-hydroxy-5-chlorocyclododecenoxide-(1,2), 3,6,11-trimethyldodecenoxide-(1,2), 3-carbomethoxycyclododecenoxide-(1,2), 4-methoxycyclododecenoxide-(1,2), 4,9-methoxycyclododecenoxide-(1,2) and 7-phenylcyclododecenoxide-(1,2).

In the process according to the invention, the oxirane compound is decomposed with ring opening so that two molecules of aldehyde are obtained from each molecule of the oxirane compound. The only exception are those oxirane compounds in which $R_1$ and $R_2$ in the above general formula I together represent an optionally substituted carbocyclic ring. In that case, ring opening is accompanied by formation of a dialdehyde. Thus, for example, in the process according to the present invention, one molecule of pentenoxide-2,3 yields one molecule of acetaldehyde and one molecule of propionaldehyde, butenoxinide-2,3 yields two molecules of acetaldehyde but cyclopentenoxide gives rise to glutaric dialdehyde and cyclohexenoxide to adipic dialdehyde.

It is not necessary to start with pure oxirane compounds. Oxirane compounds formed in situ by known reactions may also be used as starting materials for the process according to the invention.

According to the present invention, the reaction of oxirane compounds is carried out with the addition of a compound of a metal of the Groups IIIa-VIIa or Group VIII. Compounds suitable for this purpose are in particular those of the metals indium, thallium, titanium, zirconium, hafnium, vanadium, niobium, tantalum, chromium, molybdenum, tungsten, cobalt, nickel, ruthenium, rhodium, osmium, iridium and platinum, the preferred compounds being those of the metals titanium, vanadium, niobium, chromium, molybdenum, tungsten, cobalt and nickel and especially compounds of vanadium and molybdenum. The compounds of metals of the Groups IIIa-VIIa or Group VIII may be oxides, oxychlorides or salts of these metals with organic acids, preferably benzoates, naphthenates and acetyl acetonates. The following are mentioned as specific examples:

titanyl acetate, titanyl acetyl acetonate, titanyl benzoate, vanadium-(II) acetate, vanadium-(II) acetyl acetonate, vanadium-(II) benzoate, vanadium-(II) naphthenate, vanadium-(III) acetate, vanadium-(III) acetyl acetonate, vanadium-(III) benzoate, vanadium-(III) naphthenate, vanadyl acetyl acetonate, vanadyl naphthenate, niobium acetate, chromium-(II) acetate, chromium-(II) acetyl acetonate, chromium-(II) acetate, chromium-(III) acetyl acetonate, chromium-(III) naphthenate, molybdenum-(II) acetyl acetonate, molybdenum-(II) acetate, molybdenum-(II) benzoate, molybdenum-(III) acetyl acetonate, molybdenum-(III) acetate, molybdenum-(III) benzoate, molybdenum naphthenates, molybdenyl acetyl acetonates, tungsten-(III) acetate, tungstenyl acetonate, cobalt acetyl acetonate, nickel acetate, nickel benzoate, nickel naphthenate and cobalt naphthenate. Complex compounds such as carbonyls or nitrocarbonyls of a metal of the Groups IIIa-VIIa or Group VIII may also be added, e.g. molybdenum hexacarbonyl.

The quantity in which the compound of a metal of the Groups IIIa-VIIa or Group VIII is added may vary within wide limits. It is generally sufficient to add less than 10 mols-%, based on the quantity of hydrogen peroxide used, and as a rule the quantities added are in the range of from 0.01 to 10 mols-%, based on the quantity of hydrogen peroxide used, and most preferably from 0.2 to 5 mols-%. The compound of a metal of the Groups IIIa-VIIa or Group VII added may be either soluble or insoluble in the reaction mixture. The method of adding the metal compounds on inert carriers such as aluminium oxide, aluminium hydroxide, silica gel or zeolities may also be employed. It has been found advantageous also to add a compound of an alkali metal when using molybdenum compounds.

The alkali metal compounds added may be an acetate, bicarbonate, carbonate or alcoholate. These compounds are generally added in quantities of from 1 to 100% by weight, based on the quantity of the compound of a metal of the Groups IIIa-VIIa or Group VIII, preferably from 10 to 50% by weight.

The process according to the invention is generally carried out by introducing the oxirane compound and compound of a metal of the Groups IIIa-VIIa or Group VIII, if indicated together with an alkali metal compound, into the reaction vessel and adding hydrogen peroxide with stirring or by introducing hydrogen peroxide and the compound of a metal of the Groups IIIa-VIIa or Group VIII, if indicated with an alkali metal compound, into the reaction vessel and then adding the oxirane compound. The process may be carried out continuously if desired.

The molar ratio of the oxirane compound to the hydrogen peroxide in the solution of the starting materials may vary within wide limits. The oxirane compound is generally employed in an excess amounting to 1 to 200 mols-%, based on the quantity of hydrogen peroxide used, and preferably from 10 to 50 mols-%.

In the process according to the invention, the hydrogen peroxide is preferably used in the form of a non-aqueous hydrogen peroxide solution. The solvents used for hydrogen peroxide may be compounds which neither react with the oxirane compound used nor cause decomposition of hydrogen peroxide. Such solutions of hydrogen peroxide are known per se and may be obtained, for example, in accordance with the process disclosed in German Auslegeschrift No. 1.802.903. Such non-aqueous hydrogen peroxide solutions may also be obtained by adding a solvent which is miscible with water and hyrogen peroxide to an aqueous hydrogen peroxide solution and then removing the water, preferably by distillation under vacuum. Suitable hydrogen peroxide solvents for this purpose are in particular esters, N-alkyl-substituted acid amides, alcohols, carboxylic acids, sulphonic acids and phosphoric acids; the esters and alkylamides of phosphoric acids, phosphonic acids and phosphonic acids being preferred. The following are mentioned as specific examples: triethyl phosphate, dimethylmethane phosphonate, dimethyl $\beta$-cyanoethyl phosphonate, methyl $\beta$-carbomethoxy phosphonate, trioctyl phosphate and trihexyl phosphate.

It is also advantageous to use solvent mixtures which may have more suitable dissolving properties than any single solvent for simultaneously dissolving both hydrogen peroxide, the compound of a metal of the Groups IIIa-VIIa or Groups VIII, the oxirane compound and the resulting aldehyde. Thus for example one may start with a more highly concentrated solution of hydrogen peroxide in a phosphonic acid ester, for example 30% $H_2O_2$ in dimethylmethane phosphonate, and then add an inert solvent such as ethyl acetate, butyl acetate or methylene chloride to this solution. The oxirane compound and compound of a metal of the Group IIIa-VIIa or Group VIII will be more readily soluble in such a mixture.

The concentration of non-aqueous hydrogen peroxide solutions used may vary within wide limits and is fixed in practice by the explosion limit. The upper limit of hydrogen peroxide concentration is therefore from 30 to 60%, depending on the solvent used. Non-aqueous solutions of hydrogen peroxide are generally employed in concentrations of 3 to 30%, preferably 10 to 20%.

The temperature at which the process according to the invention is carried out depends generally only on the stability of hydrogen peroxide in the reaction mixture. Temperatures in the range of from $-80°$ to $+100°$ C are employed, preferably $-20°$ to $+60°$ C, depending on the nature of the compound of a metal of the Groups IIIa-VIIa or Group VIII used and on the particular solvent.

The temperature employed is determined by the vapour pressure of the reactants and of the solvent and may therefore vary within wide limits. It is not a decisive factor for the progress of the reaction.

The process according to the invention may be carried out either in the liquid or in the gaseous phase. The reaction time varies according to the oxirane compound used, the reaction temperature and the compound of a metal of the Groups IIIa-VIIa or Group VIII added. As a rule, most of the reaction will have taken place by the time the reactants are mixed and the reaction can then be completed simply by stirring.

The process according to the invention is carried out in reactors commonly used for such reactions and the catalytic action of the wall of the vessel or of foreign ions entering the solution due to corrosion must be taken into account in known manner. After termination of the reaction, the reaction mixture is worked up in known manner. In cases where the aldehyde is not yet in the free form after the reaction, it can be converted into the free aldehyde by heating, optionally with water or with an alcohol such as methanol or ethanol. The addition of acids such as sulphuric acid accelerates this process.

Methods of isolating the aldehyde are known per se; isolation may be carried out by distillation, for example by driving off the aldehyde together with steam by distillation. Aldehydes which are water-soluble can be extracted from the reaction mixture with water. Isolation from the aqueous phase is then carried out in known manner e.g. by extraction with suitable solvents as for example n-pentane or chloroform.

EXAMPLE 1

22.2 g of a 22.48% solution of $H_2O_2$ in dimethylmethane phosphonate, corresponding to 5.0 g, were added to 16.2 g of butenoxide-2,3 and 0.4 g of molybdenum-(III) acetyl acetonate at 40° C with stirring. Stirring was then continued at the same temperature. After 1½ hours, the reaction mixture had the following composition according to gas chromatographic analysis:

| acetaldehyde | 7.27 g |
|---|---|
| butane diols | 2.05 g |
| butenoxide | 3.64 g |

Analysis of butenoxide and of acetaldehyde was carried out on a 2-meter column using 15% polypropylene glycol on kieselguhr with isopropanol as internal standard, and analysis of the diols was carried out on a 2-meter column using 5% nitrile silicone on salinised kieselguhr washed with acid, with methyl benzoate as an internal standard.

EXAMPLE 2

11.4 g of a solution of hydrogen peroxide in dimethylmethane phosphonate containing 22.23% of $H_2O_2$, corresponding to 2.55 g, were added to 13.2 g of styrene oxide and 0.1 g of molybdenum-(III) acetyl acetonate at 15° C with stirring and cooling. Stirring was continued for 2 hours at 15° C after all the hydrogen peroxide had been added. Gas chromatographic analysis of the reaction mixture on a 2-meter column using 5% nitrile silicone on acid-washed silanised kieselguhr with isopropanol as internal standard, indicated a benzaldehyde content of 4.185 g. The formaldehyde content was found to be 1.35 g.

EXAMPLE 3

8.77 g of a 28.5% solution of $H_2O_2$ in dimethylmethane phosphonate, corresponding to 2.50 g of $H_2O_2$, were added to 10.78 g of cyclohexenoxide and 80 mg of vanadium-(III) acetyl acetonate at 0° C to −5° C with stirring and cooling. Stirring was continued at 0° C after all the hydrogen peroxide solution had been added. After 1 hour, the reaction mixture had the following composition:

| adipic dialdehyde | 4.385 g |
|---|---|
| trans-cyclohexanediol | 1.017 g |
| cyclohexenoxide | 6.400 g |

Analysis was carried out by quantitative gas chromatography using cyclohexyl acetate as an internal standard on a 2-meter column with 5% nitrile silicone on acid-washed kieselguhr which had been treated with dimethyl chlorosilane.

EXAMPLE 4

22.0 g of a 23.2% solution of $H_2O_2$ in dimethylmethane phosphonate, corresponding to 5.1 g, were added to 17.6 g of cyclohexenoxide and 0.4 g of molybdenum naphthenate at 38° – 45° C with stirring and cooling. The temperature was maintained at 43° C after all the hydrogen peroxide solution had been added. After 10 hours, the reaction mixture contained:

| adipic dialdehyde | 23.70%, | i.e. | 9.48 g |
|---|---|---|---|
| trans-cyclohexanediol | 8.53%, | i.e. | 3.41 g |

Analysis was carried out by gas chromatography using cyclohexyl acetate as an internal standard.

EXAMPLE 5

A 22.23% solution of $H_2O_2$ in dimethylmethane phosphonate, corresponding to 5.0 g (0.147 mol) was added dropwise to a stirred mixture of 15.12 g (0.180 mol) of cyclopentenoxide and 0.3 g of molybdenum-(III) acetyl acetonate at 45° C. Stirring was then continued for 3 hours and the following results were obtained from analysis by gas chromotography using a 2-meter separating column with 5% nitrile silicone on acid-washed silanised kieselguhr and cyclohexyl acetate as an internal standard:

| glutaric dialdehyde | 10.53 g |
|---|---|
| trans-cyclopentanediol | 1.97 g |
| cyclopentenoxide | 0.57 g |

EXAMPLE 6

18.9 g (0.225 mol) of cyclopentenoxide were added dropwise to a stirred mixture of 13.76 g of a 36.34% solution of $H_2O_2$ in dimethylmethane phosphonate and 0.2 g of molybdenum naphthenate at 45° C and stirring was then continued at the same temperature. After 3 hours, the reaction mixture analysed in the same way as described in example 5 was found to have the following composition:

| glutaric dialdehyde | 7.43 g |
|---|---|
| trans-cyclopentanediol | 1.45 g |
| cyclopentenoxide | 6.54 g |

The following analytical results were obtained after 6 hours:

| glutaric dialdehyde | 10.86 g |
|---|---|
| trans-cyclopentanediol | 2.68 g |
| cyclopentenoxide | 2.49 g |

EXAMPLE 7

11.3 g of a 22.5% solution of $H_2O_2$ in dimethylmethane phosphonate, corresponding to 2.54 g, were added dropwise at 15° C to a stirred mixture of 9.24 g of cyclopentenoxide and 0.040 g of vanadium-(III) acetyl acetonate.

After 5 hours stirring at 15° – 16° C, the reaction mixture was found to have the following composition when analysed by gas chromatography in the same way as described in example 5:

| glutaric dialdehyde | 3.79 g |
| trans-cyclopentanediol | 0.323 g |
| cyclopentenoxide | 5.95 g |

EXAMPLE 8(a)

57.5 g of an 8.70% solution of $H_2O_2$ in triethylhexyl phosphate, corresponding to 5.0 g, were added dropwise at 35° C to a stirred mixture of 15.1 g (0.180 mol) of cyclopentenoxide, 0.3 g of molybdenum-(III) acetyl acetonate and 75 mg of anhydrous potassium acetate. Stirring was continued at the same temperature after all the hydrogen peroxide solution had been added. After a reaction time of 2 hours, the reaction mixture was found to have the following composition when analysed as described in example 5:

| glutaric dialdehyde | 12.17 g |
| trans-cyclopentanediol | 1.43 g |
| cyclopentenoxide | 1.79 g |

EXAMPLE 8(b)

60 g of a reaction mixture prepared according to example 8(a) which according to analysis by gas chromatography contained 15.15% of glutaric dialdehyde was heated to boiling with 60 g of $H_2O$ for 30 minutes. The two phases were then separated and the glutaric dialdehyde content in the two phases was determined by titration. The wet chemical determination of glutaric dialdehyde was carried out in known manner by reaction with hydroxyl ammonium hydrochloride and titration of the hydrochloric acid liberated.

The following results were obtained:
1. 48.5 g of upper phase containing 1.84 g of glutaric dialdehyde
2. 71.5 g of aqueous phase containing 7.48 g of glutaric dialdehyde.

The upper phase (48.5 g) was again extracted with 48.5 g of $H_2O$, this time in the cold. The two phases were found to have the following dialdehyde contents:
48.0 g of upper phase contained 1.05% (0.50 g)
48.0 g of aqueous phase contained 3.05% (1.47 g).

EXAMPLE 9

15.5 g of a 32.2% solution of $H_2O_2$ in dimethylmethane phosphonate were added dropwise with stirring to a mixture of 5.1 g of cyclopentenoxide and 0.8 g of molybdenum-(III) acetyl acetonate at 60° C and the temperature was kept at 60° C for 3 hours after addition of the solution. The resulting reaction mixture had the following composition:

| glutaric dialdehyde | 3.36 g |
| trans-cyclopentanediol | 1.10 g |

These values were obtained by gas chromatography on a 2-meter column with 5% nitrile silicone on silanised, acid-washed kieselguhr, using cyclohexyl acetate as an internal standard.

EXAMPLE 10

7.86 g of cyclopentenoxide were added dropwise with stirring to a mixture of 38.85 g of a 6.74% solution of $H_2O_2$ in n-butyl acetate, 150 mg of molybdenum-(III) acetyl acetonate and 40 mg of potassium acetate at a temperature of 15° C and stirring was then continued for 4 hours at the same temperature.

Analysis by gas chromatography carried out in the same way as described in example 5 showed that the reaction mixture had the following composition:

| glutaric dialdehyde | 4.11 g |
| trans-cyclopentane-1,2-diol | 0.04 g |
| cyclopentoxide | 2.84 g |

What is claimed is:
1. Process for splitting oxirane compounds into aldehydes which comprises reacting an oxirane compound having the formula

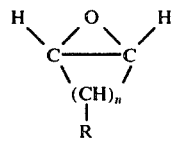

wherein
$n$ is an integer of from 3 to 10 and each of the carbon atoms determined by $n$ are substituted by R independently of each other, and
R is selected from the group of hydrogen, fluorine, $C_1$-$C_6$- alkoxy, $C_1$-$C_6$- alkyl, $C_5$-$C_7$- cycloalkyl and phenyl optionally substituted by fluorine, chlorine, or $C_1$-$C_6$ alkoxy,
with non-aqueous hydrogen peroxide in a solvent that does not react with said oxirane compound nor cause decomposition of said hydrogen peroxide, in the presence of at least one vanadium or molybdenum acetate acetyl acetonate, benzoate or naphthenate in an amount of 0.01 to 10 moles-% based on the amount of nydrogen peroxide, and at a temperature in the range of from −80° to +100° C.

2. Process of claim 1 wherein the oxirane compound is selected from the group of cyclohexenoxide and cyclopentenoxide.
3. Process of claim 1 wherein said solvent is an alcohol, acid, ester or acid alkylamide or is a hydrocarbon substituted by fluorine or chlorine or a mixture thereof.
4. Process of claim 1 wherein said solvent is an ester or alkylamide of a phosphoric acid, phosphonic acid or phosphinic acid.
5. Process of claim 1 wherein when a compound of molybdenum is used, 10 to 50% by weight, based on the quantity of molybdenum compound, of an alkali metal acetate, alkali metal bicarbonate or alkali metal carbonate are also added.

* * * * *